United States Patent
Axelson, Jr. et al.

(10) Patent No.: US 7,160,330 B2
(45) Date of Patent: Jan. 9, 2007

(54) EMULATING NATURAL KNEE KINEMATICS IN A KNEE PROSTHESIS

(75) Inventors: Stuart L. Axelson, Jr., Succasunna, NJ (US); Damon J. Servidio, Montville, NJ (US); Marcus A. Kester, Upper Saddle River, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 521 days.

(21) Appl. No.: 10/348,217

(22) Filed: Jan. 21, 2003

(65) Prior Publication Data
US 2004/0143339 A1 Jul. 22, 2004

(51) Int. Cl.
A61F 2/38 (2006.01)

(52) U.S. Cl. .................................. 623/20.14

(58) Field of Classification Search ............ 623/16.11, 623/18.11, 20.14, 20.15, 20.21, 20.23, 20.24, 623/20.26, 20.27, 20.31, 20.32, 20.34, 20.35, 623/20.36
See application file for complete search history.

(56) References Cited

U.S. PATENT DOCUMENTS

| | | | |
|---|---|---|---|
| 5,133,758 A | | 7/1992 | Hollister |
| 5,147,405 A | * | 9/1992 | Van Zile et al. ......... 623/20.27 |
| 5,326,361 A | * | 7/1994 | Hollister ................. 623/20.31 |
| 5,370,699 A | * | 12/1994 | Hood et al. ............. 623/20.28 |
| 5,824,100 A | * | 10/1998 | Kester et al. ............ 623/20.31 |
| 6,039,764 A | * | 3/2000 | Pottenger et al. ........ 623/20.32 |
| 6,406,497 B1 | * | 6/2002 | Takei ..................... 623/20.31 |
| 6,699,291 B1 | * | 3/2004 | Augoyard et al. ....... 623/20.27 |

OTHER PUBLICATIONS

Howmedica, "Duracon Total Knee System," undated, covers and pp. 12, 13.

Wright Medical Technology, "Advance Knee System," undated, pp. 1-5.

"Duraconfidence," Field Bulletin, No. #K39-112700, dated Nov. 27, 2000, two pages.

"The PCL and Roll-Back" (as produced from Controversies in knee replacement. Laskin, R., ed. Oxford: Oxford University Press, 2001, pp. 49-54.

* cited by examiner

*Primary Examiner*—Eduardo C. Robert
*Assistant Examiner*—Anuradha Ramana
(74) *Attorney, Agent, or Firm*—Arthur Jacob

(57) ABSTRACT

A knee prosthesis and method for emulating movements, during flexion, of a natural knee joint replaced by the knee prosthesis, by enabling engagement and relative movement between the femoral component and the tibial component of the knee prosthesis along arcuate tracks, including rotational movement about a longitudinal axis of rotation, during flexion about a transverse axis of rotation, and maintaining the transverse axis of rotation essentially in a generally medial-lateral longitudinal plane maintained in close proximity with a generally coronal plane passing through the centers of curvature of the arcuate tracks during flexion within at least a prescribed range of flexion extending from about 0° of flexion to a predetermined degree of flexion, preferably about 60° of flexion. A stabilizing mechanism couples the femoral component with the tibial component within a portion of the prescribed range of flexion, the portion being between about 45° of flexion and about 60° of flexion, for providing stability and for assisting in maintaining the transverse axis of rotation essentially in the longitudinal plane, and the longitudinal plane in close proximity with the coronal plane as the longitudinal plane is rotated about the longitudinal axis of rotation.

60 Claims, 7 Drawing Sheets

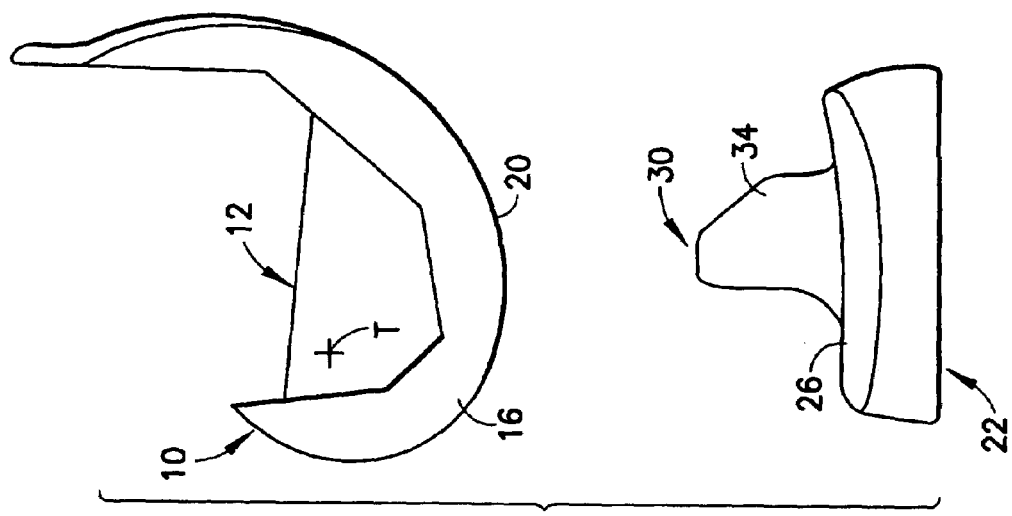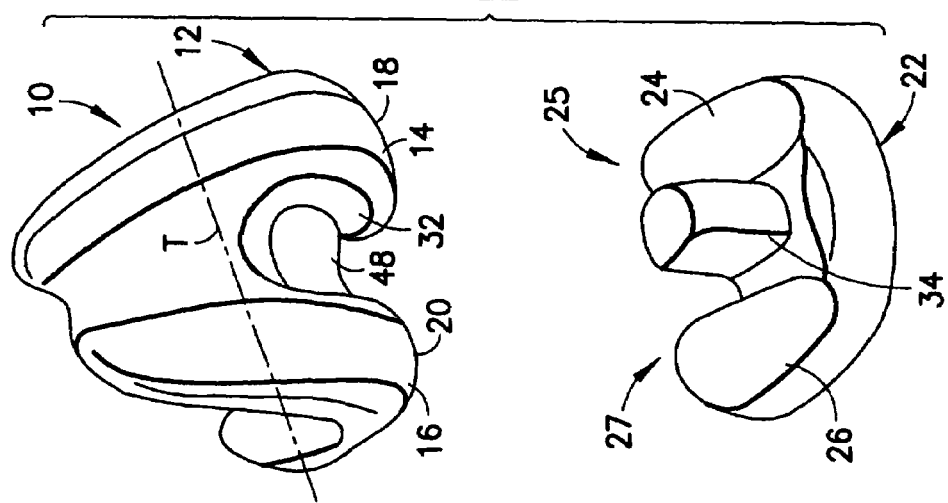

EMULATING NATURAL KNEE KINEMATICS IN A KNEE PROSTHESIS

BACKGROUND OF THE INVENTION

1. Field of the Invention

The present invention relates generally to the replacement of a natural knee joint with a knee prosthesis and pertains, more specifically, to achieving better emulation of natural knee joint kinematics in a prosthetic knee.

During articulation of a natural knee joint, flexion between the tibia and the femur takes place about a transverse axis while, at the same time, some relative rotation between the tibia and the femur occurs about a longitudinal axis. Such flexion and rotation is necessary to carry out a normal gate cycle. It has been established that in full extension the tibia is rotationally displaced, relative to the femur, by approximately 2° to 3°. As the natural knee flexes, the tibia rotates internally. According to previous studies, about 5° of rotation ordinarily occurs as the knee is articulated from 0° to 10° of flexion; thereafter, little further rotation occurs up to at least about 45° of flexion. Total rotation at 110° of flexion is approximately 20°.

2. Description of the Related Prior Art

Rotational stability of the natural knee is provided by the collateral and cruciate ligaments. The cruciate ligaments deter uncontrolled internal rotation within a certain range of flexion of the knee, while the collateral ligaments provide transverse stability and deter uncontrolled external rotation of the tibia. Where the natural knee is replaced by a total knee prosthesis, either the anterior cruciate ligament or both the anterior and posterior cruciate ligaments ordinarily are sacrificed. In these instances, the knee prosthesis usually is provided with tibiofemoral articular constraint to supply the stability ordinarily provided by the sacrificed anterior cruciate ligament and a stabilizing mechanism for supplying the stability ordinarily provided by the sacrificed posterior cruciate ligament.

BRIEF SUMMARY OF THE INVENTION

The present invention provides an improvement, both in construction and in procedure, which enables a knee prosthesis more closely to mimic the movements of the natural knee for smooth knee kinematics. As such, the present invention attains several objects and advantages, some of which are summarized as follows: Provides a knee prosthesis which better emulates movements of the natural knee for smooth knee flexion and extension; allows a recipient of a total knee prothesis to flex the knee easily and with less effort, while offering smooth prosthetic knee kinematics; enables the implant of a knee prosthesis utilizing current known surgical techniques while providing better prosthetic knee kinematics; provides a recipient of a total knee replacement with greater comfort and increased confidence in accommodating to the replacement; enables a more accurate emulation of the natural knee with a prosthetic knee having relatively few component parts, all of which are configured for simplified manufacture; provides an effective replacement for the natural knee, exhibiting exemplary performance over an extended service life.

The above objects and advantages, as well as further objects and advantages, are attained by the present invention which may be described briefly as providing, in a knee prosthesis for implantation to replace a natural knee joint and emulate movements of the natural knee joint during articulation, the natural knee joint having a lateral compartment and a medial compartment, the knee prosthesis having a femoral component including at least one condylar element with a condylar surface having a transverse axis of rotation, and a tibial component including at least one articular surface for engagement with the condylar surface of the femoral component in one of the lateral and medial compartments for articulation of the knee prosthesis through flexion about the transverse axis of rotation; an improvement wherein the condylar surface and the articular surface are configured for enabling engagement between the condylar surface and the articular surface along a generally arcuate track during articulation about the transverse axis of rotation for flexion within at least a prescribed range of flexion extending up to a predetermined degree of flexion while enabling relative rotational movement between the femoral component and the tibial component to take place about a longitudinal axis of rotation, the generally arcuate track having a center of curvature placed in a generally coronal plane, and the longitudinal axis of rotation being located essentially in a generally sagittal plane intersecting the coronal plane at an intersection, and being spaced a predetermined distance from the intersection such that upon flexion within the prescribed range of flexion, the transverse axis of rotation will be maintained essentially in a generally medial-lateral longitudinal plane located in close proximity with the coronal plane, with the longitudinal plane spaced from the longitudinal axis of rotation essentially by the predetermined distance and movable about the longitudinal axis of rotation in response to relative rotational displacement between the femoral component and the tibial component, to intersect the coronal plane at angles corresponding to the relative rotational displacement during flexion within the prescribed range of flexion.

In addition, the present invention provides, in a knee prosthesis for implantation to replace a natural knee joint and emulate movements of the natural knee joint during articulation, the knee prosthesis having a lateral compartment and a medial compartment, a femoral component including a lateral condylar element with a lateral condylar surface, a medial condylar element with a medial condylar surface, and a transverse axis of rotation, and a tibial component including a lateral articular surface for engagement with the lateral condylar surface of the femoral component in the lateral compartment and a medial articular surface for engagement with the medial condylar surface of the femoral component in the medial compartment for articulation of the knee prosthesis through flexion about the transverse axis of rotation: an improvement wherein the condylar surfaces and the articular surfaces are configured for enabling engagement between the lateral condylar surface and the lateral articular surface at positions along a first generally arcuate track having a first center of curvature and between the medial condylar surface and the medial articular surface at positions along a second generally arcuate track having a second center of curvature during articulation about the transverse axis of rotation for flexion within at least a prescribed range of flexion extending up to a predetermined degree of flexion while enabling relative rotational movement between the femoral component and the tibial component to take place about a longitudinal axis of rotation, the first and second centers of curvature being placed in a common generally coronal plane, and the longitudinal axis of rotation being located essentially in a generally sagittal plane intersecting the coronal plane at an intersection and being spaced a predetermined distance from the intersection such that upon if flexion within the pesercribed range of flexion the transverse axis of rotation will be maintained essentially in a generally medial-lateral longitudinal plane located in close proximity with the coronal plane, and the longitudinal plane spaced from the longitudinal axis of rotation essentially by the predetermined distance and movable about the longitudinal axis of rotation in response to relative rotational displacement between the femoral component and the tibial component, to intersect the coronal plane at angles corresponding to the relative rotational displacement during flexion within the prescribed range of flexion.

Further, the present invention provides a method for emulating movements of a natural knee joint in a knee prosthesis upon implantation of the knee prosthesis to replace the natural knee joint, the natural knee joint having a lateral compartment and a medial compartment, the knee prosthesis including a femoral component having at least one condylar element with a condylar surface having a transverse axis of rotation and a tibial component including at least one articular surface for engagement with the condylar surface of the femoral component for articulation of the knee prosthesis through flexion about the transverse axis of rotation, the condylar surface and the articular surface being located in the one of the lateral and medial compartments upon implant of the knee prosthesis, the method comprising: enabling engagement between the condylar surface and the articular surface at positions along a generally arcuate track having a center of curvature; placing the center of curvature in a generally coronal plane; enabling relative rotational movement between the femoral component and the tibial component during articulation about the transverse axis of rotation for flexion within at least a prescribed range of flexion extending up to a predetermined degree of flexion while enabling relative rotational movement between the femoral component and the tibial component to take place about a, longitudinal axis of rotation located essentially in a generally sagittal plane intersecting the coronal plane at an intersection and spaced a predetermined distance from the intersection; and maintaining the transverse axis of rotation in a generally medial-lateral longitudinal plane located in close proximity with the coronal plane, with the longitudinal plane spaced from the longitudinal axis of rotation essentially by the predetermined distance while moving the longitudinal plane about the longitudinal axis of rotation in response to relative rotational displacement between the femoral component and the tibial component, to intersect the coronal plane at angles corresponding to the relative rotational displacement during flexion within the prescribed range of flexion.

Still further, the present invention provides a method for emulating movements of a natural knee joint in a knee prosthesis upon implantation of the knee prosthesis to replace the natural knee joint, the knee prosthesis having a lateral compartment and a medial compartment, a femoral component including a lateral condylar element with a lateral condylar surface, a medial condylar element with a medial condylar surface, and a transverse axis of rotation, and a tibial component including a lateral articular surface for engagement with the lateral condylar surface of the femoral component in the lateral compartment and a medial articular surface for engagement with the medial condylar surface of the femoral component in the medial compartment for articulation of the knee prosthesis through flexion about the transverse axis of rotation, the method comprising: enabling engagement between the lateral condylar surface and the lateral articular surface along a first generally arcuate track having a first center of curvature; enabling engagement between the medial condylar surface and the medial articular surface along a second generally arcuate track having a second center of curvature; placing the first and second centers of curvature in a generally coronal plane; enabling relative rotational movement between the femoral component and the tibial component during articulation about the transverse axis of rotation for flexion within at least a prescribed range of flexion extending up to a predetermined degree of flexion while enabling relative rotational movement between the femoral component and the tibial component to take place about a longitudinal axis of rotation located essentially in a generally sagittal plane intersecting the coronal plane at an intersection and spaced a predetermined distance from the intersection; and maintaining the trans-verse axis of rotation in a generally medial-lateral longitudinal plane located in close proximity with the coronal plane, with the longitudinal plane spaced from the longitudinal axis of rotation essentially by the predetermined distance while moving the longitudinal plane about the longitudinal axis of rotation in response to relative rotational displacement between the femoral component and the tibial component, to intersect the coronal plane at angles corresponding to the relative rotational displacement during flexion within the prescribed range of flexion.

BRIEF DESCRIPTION OF THE SEVERAL VIEWS OF THE DRAWING

The invention will be understood more fully, while still further objects and advantages will become apparent, in the following detailed description of preferred embodiments of the invention illustrated in the accompanying drawing, in which:

FIG. 1 is an exploded perspective view showing portions of a knee prosthesis constructed in accordance with the present invention;

FIG. 2 is an exploded side elevational view of the portions of the knee prosthesis;

DETAILED DESCRIPTION OF THE INVENTION

Figure 3:
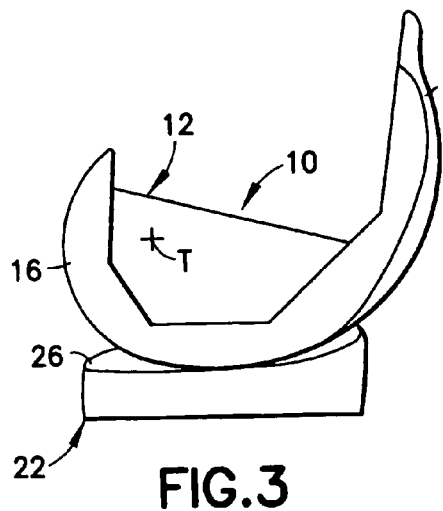
FIG. 3 is a side elevational view of the portions of the knee prosthesis showing the femoral component of the prosthesis engaged with the tibial component, at 0° of flexion.
Figure 4:
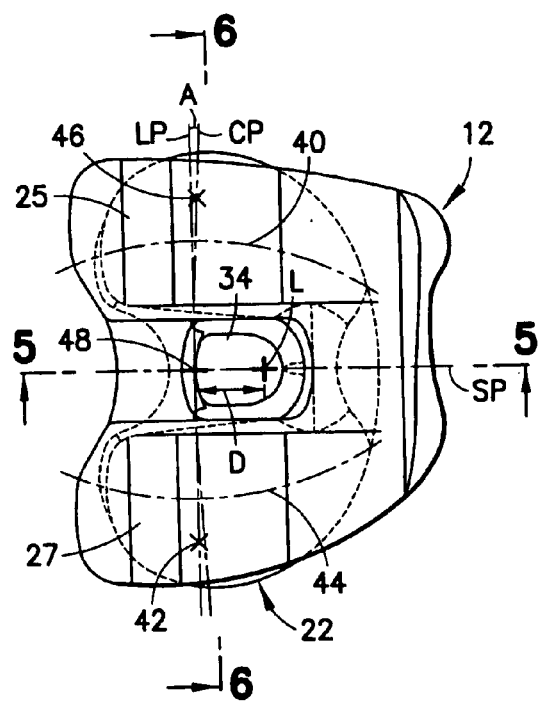
FIG. 4 is a partially diagrammatic top plan view of the prosthesis in the position shown in FIG. 3.
Figure 5:
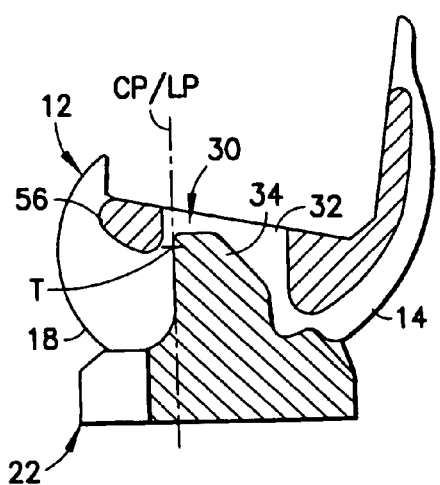
FIG. 5 is a cross-sectional view taken along line 5—5 of FIG. 4.

Referring now to the drawing, and especially to FIGS. 1 and 2 thereof, a knee prosthesis constructed in accordance with the present invention is shown at 10 and is seen to include a femoral component 12 having condylar elements illustrated in the form of condyles including a lateral condyle 14 and a medial condyle 16. Each condyle 14 and 16 includes a condylar surface 18 and 20, respectively, and the condylar surfaces 18 and 20 have a common axis of rotation T extending transversely across the femoral component 12. In the preferred embodiment, axis of rotation T is located on the femoral component 12 such that upon implant of the knee prosthesis 10, axis of rotation T will be coincident with a line extending transversely between the medial and lateral ligament attachment points on the femur of the natural knee. A tibial component 22 has articular surfaces including a lateral articular surface 24 for engagement with lateral condylar surface 18 of lateral condyle 14, within a lateral compartment 25 of the knee prosthesis 10, and a medial articular surface 26 for engagement with medial condylar surface 20 of medial condyle 16, within a medial compartment 27 of the knee prosthesis 10.

Knee prosthesis 10 is to serve as a total replacement for a natural knee joint. In the total knee replacement provided by knee prosthesis 10, both the anterior and the posterior cruciate ligaments are sacrificed, and knee prosthesis 10 includes a stabilizing mechanism 30 for stabilizing the engagement between the lateral condyle 14 and the lateral articular surface 24, and between the medial condyle 16 and the medial articular surface 26, during articulation of the knee prosthesis 10 within the range of articulation in which the posterior cruciate ligament ordinarily would provide stability in the natural knee. Stabilizing mechanism 30 includes a stabilizing compartment 32 on the femoral component 12, between the condyles of the femoral component 12, the compartment 32 preferably being located intermediate the lateral condyle 14 and the medial condyle 16 of the femoral component 12, and a stabilizing post 34 on the tibial component 22, between the articular surfaces of the tibial component 22, the post 34 preferably being located intermediate the lateral articular surface 24 and the medial articular surface 26 of the tibial component 22, for projecting in a superior direction into the stabilizing compartment 32, in a manner known in posterior stabilized prosthetic knee implants.

Figure 6:
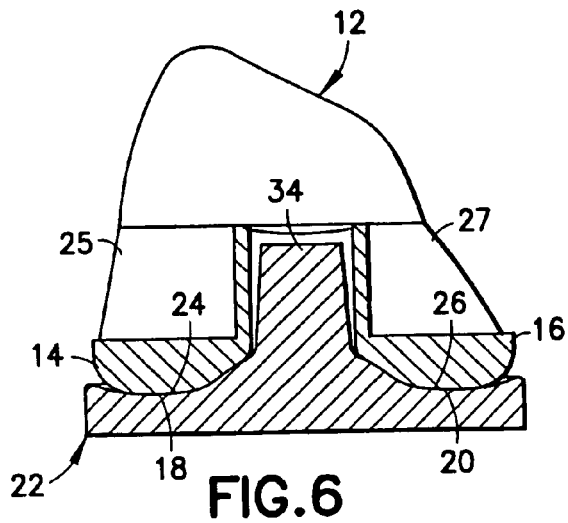
FIG. 6 is a cross-sectional view taken along line 6—6 of FIG. 4.
Figure 7:
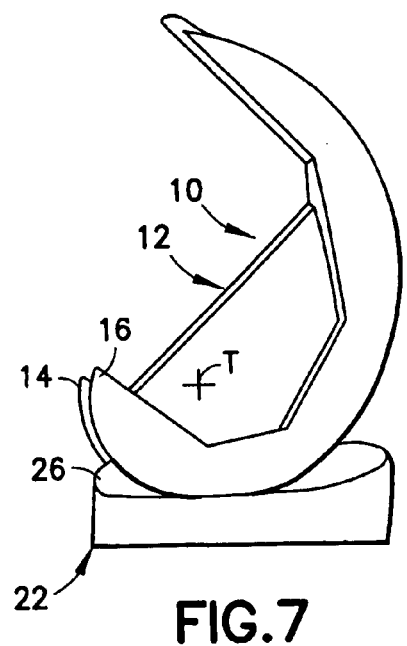
FIGS. 7 through 10 are views similar to FIGS. 3 through 6, respectively, but showing the components at 45° of flexion.
Figure 15:
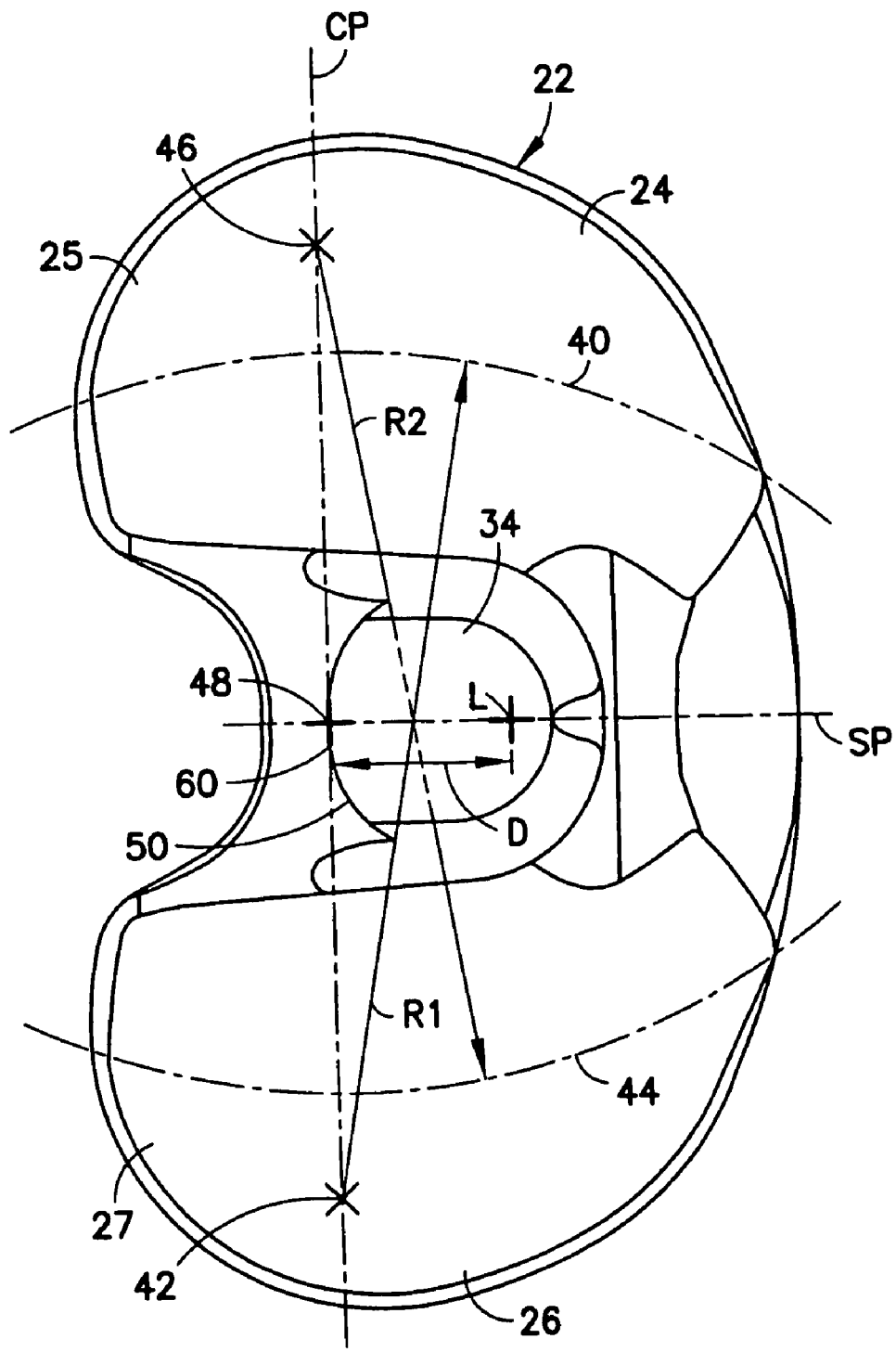
FIG. 15 is an enlarged, partially diagrammatic top plan view of the tibial component.
Figure 16:
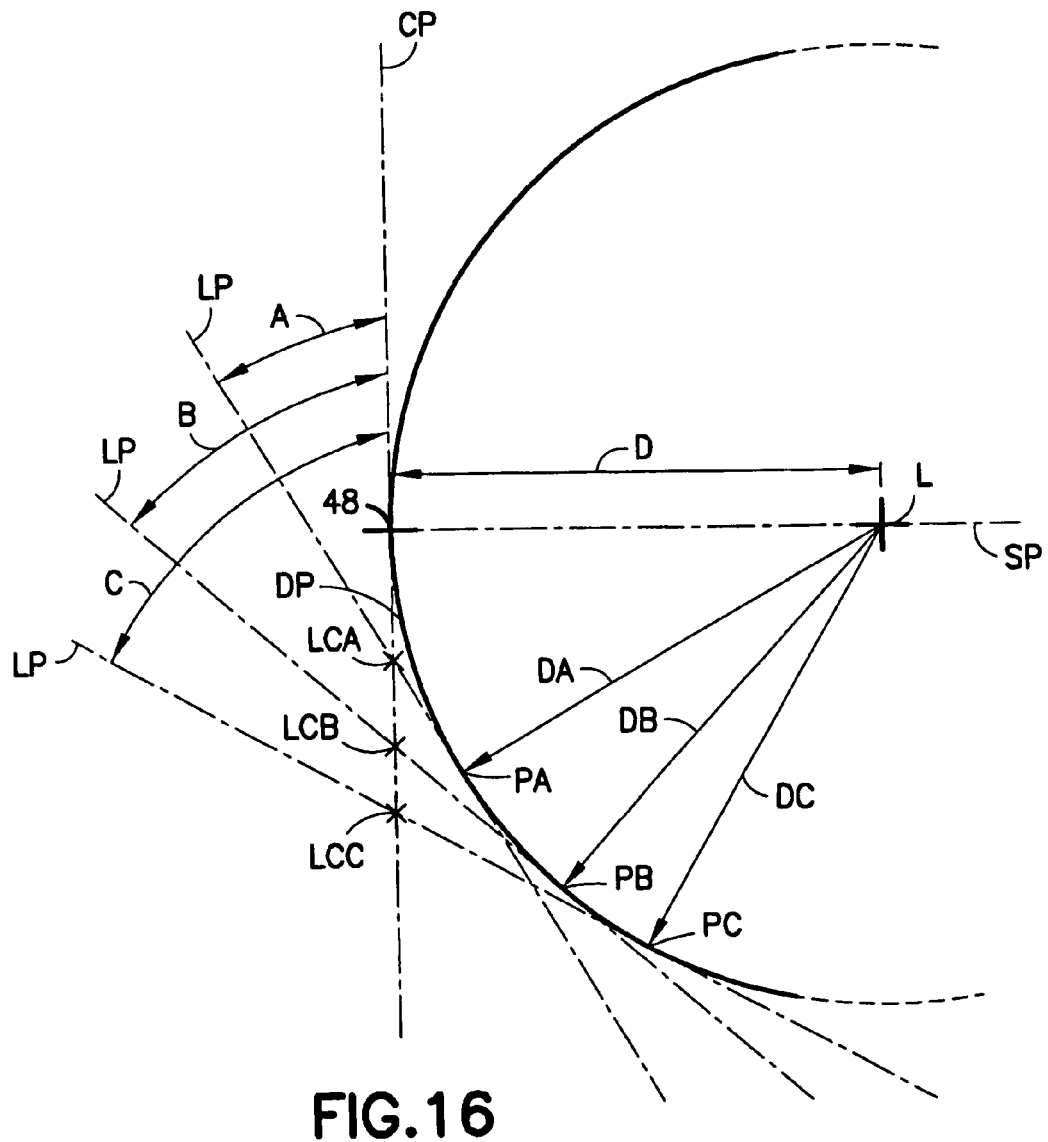
FIG. 16 is a position diagram, with relative proportions modified and exaggerated to better show positions illustrated in FIGS. 3 through 14.

Turning now to FIGS. 3 through 6, viewed in conjunction with FIGS. 15 and 16, knee prosthesis 10 is illustrated at 0° of flexion, and the condylar surfaces of the condyles of the femoral component 12 are engaged with the articular surfaces of the tibial component 22. The condylar surfaces 18 and 20 and the articular surfaces 24 and 26 are configured such that upon implantation of the knee prosthesis 10, relative rotational movement between the femoral component 12 and the tibial component 22 during articulation of the knee prosthesis 10 better emulates the relative rotation observed in the natural knee. Thus, engagement between lateral condylar surface 18 and lateral articular surface 24 is so complementary, and preferably essentially congruent, as illustrated by the profile configuration contours shown in FIG. 6, at positions along a first generally arcuate track 40 having a first center of curvature 42 located in the medial compartment 27, and engagement between medial condylar surface 20 and medial articular surface 26 is so complementary, and preferably essentially congruent, as illustrated in FIG. 6, along a second arcuate track 44 having a second center of curvature 46 located in the lateral compartment 25, that the relative configurations of the condylar surfaces 18 and 20 and the articular surfaces 24 and 26 will enable relative rotational movement between the femoral component 12 and the tibial component 22 in such a manner as to emulate the relative rotation observed in the natural knee during articulation about the transverse axis T.

In order to achieve such emulation, the first and second centers of curvature 42 and 46 are placed in a common generally coronal plane CP. The relative rotation takes place about a longitudinal axis of rotation L located essentially in a generally sagittal plane SP which intersects the coronal plane CP at an intersection 48. Longitudinal axis L is spaced from intersection 48 in the posterior direction by a predetermined distance D. The transverse axis of rotation T is placed essentially in a generally medial-lateral longitudinal plane LP, shown in FIG. 4 oriented at an angle A to coronal plane CP, angle A representing a relative rotational displacement between the femoral component 12 and the tibial component 22 of approximately 2° to 3°, at 0° of flexion, in response to relative rotation between the femoral component 12 and the tibial component 22. The longitudinal plane LP is shown in close proximity with coronal plane CP, intermediate the lateral and medial compartments 25 and 27, the longitudinal plane LP being shown intersecting the coronal plane CP very near to the intersection 48 between the coronal plane CP and the sagittal plane SP. The intersection 48 is shown in a preferred location, at the midpoint between the first and second centers of curvature 42 and 46, with longitudinal plane LP being otherwise closely adjacent coronal plane CP. In the preferred construction, rotation of the longitudinal plane LP is about longitudinal axis L, with the longitudinal plane LP maintained essentially tangent with an arcuate path DP at a point of tangency PA and distance D serving as a constant radius of rotation, illustrated at DA. Thus, angle A represents the very small angular distance between the point of tangency PA and the intersection 48, and illustrates the even smaller distance between the intersection 48 and the intersection LCA between the longitudinal plane LP and the coronal plane CP. Distance D is determined empirically, the predetermined distance D being a measure of the posterior spacing of the flexion axis from the longitudinal axis of rotation observed in the natural knee.

Figure 8:
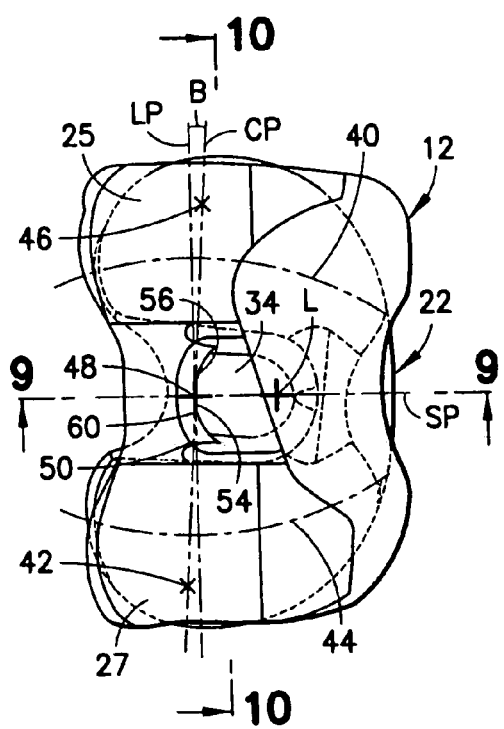
Figure 9:
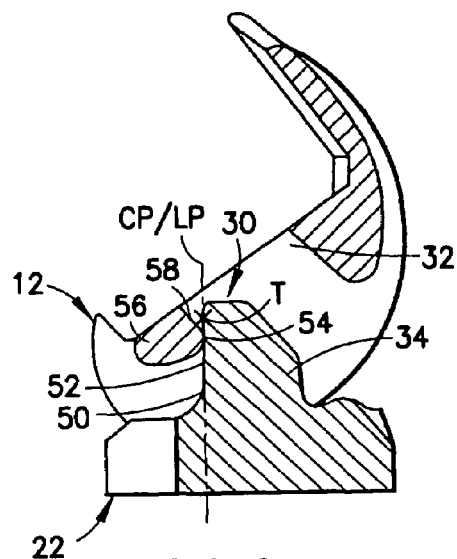
Figure 10:
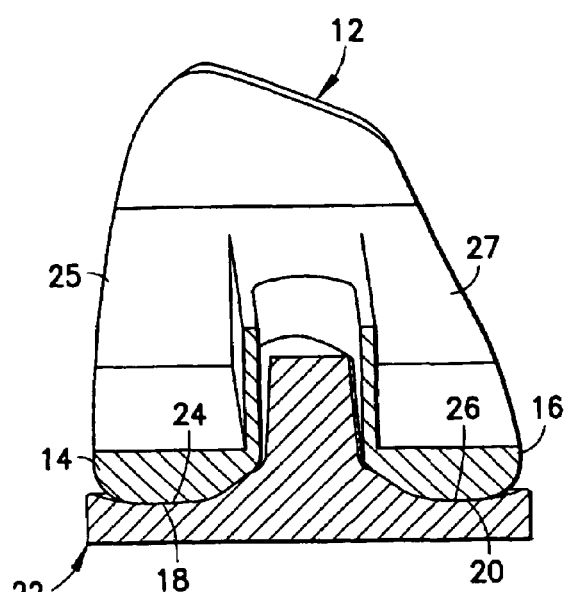
Figure 11:
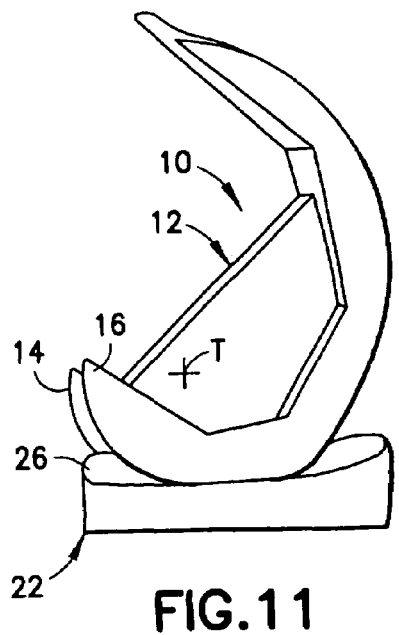
FIGS. 11 through 14 are views similar to FIGS. 3 through 6, respectively, but showing the components at 60° of flexion.

As shown in FIGS. 7 through 10, viewed in conjunction with FIGS. 15 and 16, knee prosthesis 10 is at 45° of flexion. During articulation from 0° of flexion to 45° of flexion, the relative configurations of the condylar surfaces 18 and 20 and the respective articular surfaces 24 and 26, including the preferred essentially congruent profile contour configurations illustrated in FIG. 10, have enabled relative rotational engagement at positions along arcuate tracks 40 and 44, and rotational movement between the femoral component 12 and the tibial component 22 about the longitudinal axis of rotation L, as illustrated in FIG. 8 by an angle B between the longitudinal plane LP and coronal plane CP, angle B representing a preferred rotational displacement between the femoral component 12 and the tibial component 22 of about 4° to 5° of rotation. At the same time, the relative configurations of the condylar surfaces 18 and 20 and the articular surfaces 24 and 26 have maintained the transverse axis of rotation T essentially within the longitudinal plane LP and have maintained the longitudinal plane LP in close proximity with coronal plane CP intermediate the lateral and medial compartments 25 and 27, with longitudinal plane LP preferably intersecting coronal plane CP very near to the intersection 48, which preferably is placed at the midpoint between the centers of curvature 42 and 46. With distance D serving as a radial distance DB and the longitudinal plane LP maintained essentially tangent to the arcuate path DP, the angular distance between intersection 48 and point of tangency PB, as represented by angle B, is very small and the distance between the intersection LCB of longitudinal plane LP with coronal plane CP and intersection 48 is even smaller. Longitudinal plane LP is otherwise maintained closely adjacent coronal plane CP.

Figure 12:
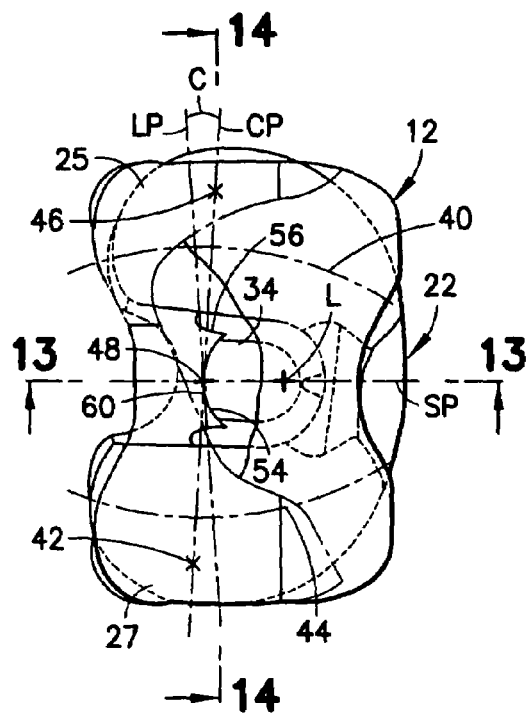
Figure 13:
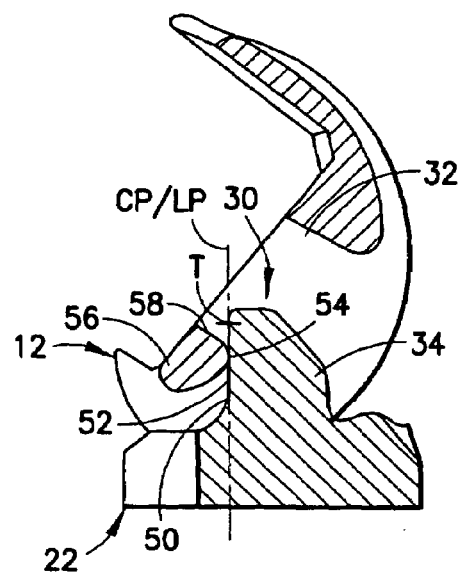
Figure 14:
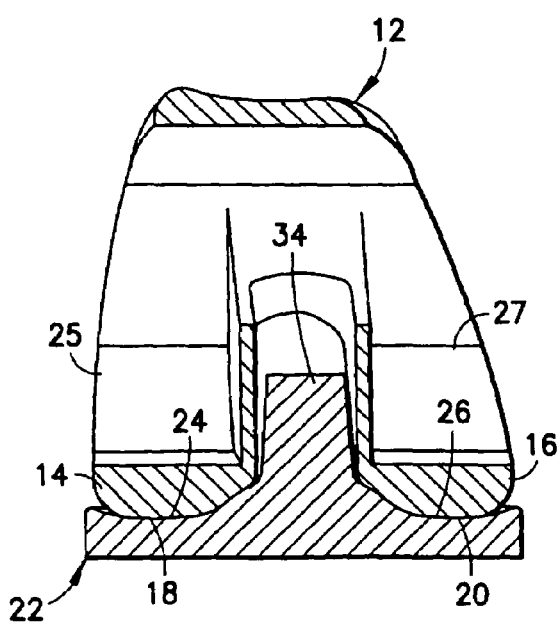

As shown in FIGS. 11 through 14, viewed in conjunction with FIGS. 15 and 16, knee prosthesis 10 is at 60° of flexion. During flexion of knee prosthesis 10 from 45° of flexion, as illustrated in FIGS. 7 through 10, to 60° of flexion, the relative configurations of the condylar surfaces 18 and 20 and the respective articular surfaces 24 and 26 have enabled engagement and relative movement along arcuate tracks 40 and 44, and relative rotational displacement between the femoral component 12 and the tibial component 22 in response to relative rotational movement between the femoral component 12 and the tibial component 22 about the longitudinal axis of rotation L, as illustrated in FIG. 12 by an angle C between longitudinal plane LP and coronal plane CP. At the same time, the relative configurations of the condylar surfaces 18 and 20 and the articular surfaces 24 and 26, including the profile contour configurations shown in FIG. 14, have maintained the transverse axis of rotation T essentially within the longitudinal plane LP, and have maintained the longitudinal plane LP in close proximity with coronal plane CP, intermediate the lateral and medial compartments 25 and 27, with longitudinal plane LP preferably intersecting coronal plane CP at intersection LCC, very near to the intersection 48, which intersection 48 preferably is placed at the midpoint between the centers of curvature 42 and 46, and otherwise closely adjacent coronal plane CP. As before, longitudinal plane LP preferably is maintained essentially tangent to arcuate path DP, at a point of tangency PC spaced radially from longitudinal axis L a distance DC, preferably equivalent to distance D. The angular distance between the intersection 48 and point of tangency PC, as represented by angle C, is very small and the distance between the intersection LCC of the longitudinal plane LP with coronal plane CP and intersection 48 is even smaller.

In addition, during flexion from 45° of flexion to 60° of flexion, stabilizing mechanism 30 couples femoral component 12 with tibial component 22 to supply stability ordinarily provided in the natural knee by the posterior cruciate ligament, which cruciate ligament now is sacrificed. Thus, the post 34 projects upwardly, in the superior direction, into the stabilizing compartment 32 for coupling the femoral component 12 with the tibial component 22. The stabilizing mechanism 30 includes a cam surface 50 on the posterior aspect of the post 34, shown in the form of a posterior face 52 of post 34, and a follower surface 54 at an anterior aspect of a follower 56, shown in the form of an anterior face 58 of follower 56 extending transversely across the interior of the stabilizing compartment 32. The relative contour configurations of the cam surface 50 and the follower surface 54 enable relative rotation between the femoral component 12 and the tibial component 22 about longitudinal axis of rotation L to continue, to angle C between the longitudinal plane LP and coronal plane CP. At the same time, stabilizing mechanism 30 assists in maintaining the transverse axis of rotation T essentially in the longitudinal plane LP, and assists in maintaining longitudinal plane LP in close proximity with coronal plane CP, as flexion continues between 45° of flexion and 60° of flexion, as set forth above.

As described above, the transverse axis of rotation T is maintained essentially in the longitudinal plane LP during articulation through a prescribed range of flexion extending up to a predetermined degree of flexion. In the preferred embodiment illustrated in the form of knee prosthesis 10, the predetermined degree of flexion is about 60° of flexion and the prescribed range of flexion extends between about 0° of flexion and about 60° of flexion. In a portion of the prescribed range of flexion, shown as the portion between about 45° of flexion and about 60° of flexion, the stabilizing mechanism 30 couples femoral component 12 with tibial component 22 to supply stability ordinarily provided in the natural knee by the posterior cruciate ligament while, at the same time, assisting in maintaining the transverse axis of rotation T essentially in the longitudinal plane LP, and the longitudinal plane LP in close proximity with the coronal plane CP, intermediate the lateral and medial compartments 25 and 27, with longitudinal plane LP preferably intersecting the coronal plane CP, very near to intersection 48. To this end, the first and second centers of curvature 42 and 46 are located so that coronal plane CP is tangent to cam surface 50 at the intersection 48, and the intersection 48 is located at the midpoint between the centers of curvature 42 and 46. In addition, in the preferred construction the radius R1 of arcuate track 40 is equal to the radius R2 of arcuate track 44 so that the arcuate tracks 40 and 44 are essentially symmetrical about the intersection 48. Beyond 60° of flexion, engagement between the cam surface 50 and follower surface 54 induces rollback, and the transverse axis of rotation T is moved away from the coronal plane CP, in the posterior direction.

Further, as described above in connection with FIGS. 3 through 14 and 16, the tibial component 22 is displaced through angle C relative to femoral component 12, as the knee prosthesis 10 is articulated through the prescribed range of flexion, between about 0° of flexion and about 60° of flexion. The rotational displacement represented by angle C preferably is about 6° of rotation in an internal direction. As best seen in FIGS. 8 and 12, longitudinal plane LP is maintained essentially tangent to cam surface 50 along a segment 60, where the follower surface 54 engages the cam surface 50, throughout the portion of the prescribed range of if flexion in which the stabilizing mechanism 30 couples the femoral component 12 with the tibial component 22, that is, between about 45° of flexion and about 60° of flexion. As set forth above, the centers of curvature 42 and 44 are located so that coronal plane CP is tangent to cam surface 50 at the intersection 48, preferably located at the midpoint between the centers of curvature 42 and 44. Segment 60 of cam surface 50 preferably is located along a cylindrical surface having a constant radius extending from the longitudinal axis L to cam surface 50, shown as DA, DB, and DC in FIG. 16, the radius preferably being essentially equal to the predetermined distance D, thereby maintaining an essentially constant distance between the longitudinal axis L, and the longitudinal plane LP, that distance being equivalent to distance D. Longitudinal plane LP is maintained tangent to cam surface 50 at a respective point of tangency, shown in FIG. 16 as PA, PB and PC, located very near to the intersection 48 of sagittal plane SP and coronal plane CP, the angular distance between intersection 48 and the point of tangency PA, PB and PC at 0°, 45° and 60° of flexion, respectively, as represented by angles A, B and C, respectively, being very small. The distance between the intersection of the longitudinal plane LP with the coronal plane CP, as shown by LCA, LCB and LCC in FIG. 16, and intersection 48 is even smaller. In this manner, articulation of knee prosthesis 10 mimics articulation of the natural knee within the prescribed range of flexion for better emulation of natural knee joint kinematics in knee prosthesis 10.

It will be appreciated that in view of the differences which exist in the physical characteristics and conditions encountered among the various recipients of knee implants, and the necessity for providing a finite number of sizes and configurations in femoral components and in tibial components to accommodate the needs of a particular recipient, as well as the nature and exigencies of surgery, the ideally precise relationships among the various engaged surfaces, axes and planes cannot always be realized fully in every recipient. Accordingly, the terms "about", "essentially" and "generally", as applied to the description of ranges of movement, the relationship between engaged condylar and articular surfaces, between axes and planes, and in the relative orientation of other elements of the described construction are meant to indicate that some departure from ideally precise relationships may be present without departing from the basic combination of elements which constitute the improvement of the present invention. Likewise, use of the terms "close proximity", "closely adjacent", "very small" and "very near" in referring to relationships between the longitudinal plane LP and the coronal plane CP is meant to encompass a combination of elements wherein some departure from an ideal relationship in which the position of the planes relative to one another is most effective is accommodated while still attaining the objects and advantages of the present invention.

It will be seen that the present invention attains the several objects and advantages summarized above, namely: Provides a knee prosthesis which better emulates movements of the natural knee for smooth knee flexion and extension; allows a recipient of a total knee prosthesis to flex the knee easily and with less effort, while offering smooth prosthetic knee kinematics; enables the implant of a knee prosthesis utilizing current known surgical techniques while providing better prosthetic knee kinematics; provides a recipient of a total knee replacement with greater comfort and increased confidence in accommodating to the replacement; enables a more accurate emulation of the natural knee with a prosthetic knee having relatively few component parts, all of which are configured for simplified manufacture; provides an effective replacement for the natural knee, exhibiting exemplary performance over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. In a knee prosthesis for implantation to replace a natural knee joint and emulate movements of the natural knee joint during articulation, the natural knee joint having a lateral compartment and a medial compartment, the knee prosthesis having a femoral component including at least one condylar element with a condylar surface having a transverse axis of rotation, and a tibial component including at least one articular surface for engagement with the condylar surface of the femoral component in one of the lateral and medial compartments for articulation of the knee prosthesis through flexion about the transverse axis of rotation:

an improvement wherein the condylar surface and the articular surface are configured for enabling engagement between the condylar surface and the articular surface along a generally arcuate track during articulation about the transverse axis of rotation for flexion within at least a prescribed range of flexion extending up to a predetermined degree of flexion while enabling relative rotational movement between the femoral component and the tibial component to take place about a longitudinal axis of rotation, the generally arcuate track having a center of curvature placed in a generally coronal plane, and the longitudinal axis of rotation being located essentially in a generally sagittal plane intersecting the coronal plane at an intersection, and being spaced a predetermined distance from the intersection such that upon flexion within the prescribed range of flexion the transverse axis of rotation will be maintained essentially in a generally medial-lateral longitudinal plane located in close proximity with the coronal plane, with the longitudinal plane spaced from the longitudinal axis of rotation essentially by the predetermined distance and movable about the longitudinal axis of rotation in response to relative rotational displacement between the femoral component and the tibial component, to intersect the coronal plane at angles corresponding to the relative rotational displacement during if flexion within the prescribed range of flexion.

2. The improvement of claim 1 wherein the coronal plane is spaced posteriorly from the longitudinal axis of rotation, and the longitudinal plane rotates about the longitudinal axis of rotation along an arcuate path having a radius essentially equivalent to the predetermined distance during flexion within the prescribed range of flexion.

3. The improvement of claim 2 wherein the longitudinal plane is maintained essentially tangent to the arcuate path during flexion within the prescribed range of flexion.

4. The improvement of claim 1 wherein the prescribed range of flexion extends between about 0° of flexion and a predetermined degree of flexion of about 60° of flexion.

5. The improvement of claim 1 wherein the condylar surface and the articular surface are configured for enabling essentially congruent engagement during movement throughout the generally arcuate track.

6. The improvement of claim 1 wherein the center of curvature is located for placement in the other of the lateral and medial compartments.

7. The improvement of claim 1 wherein the knee prosthesis includes a medial compartment and a lateral compartment spaced laterally from the medial compartment, the one condylar element is located in the lateral compartment of the knee prosthesis, and the center of curvature of the generally arcuate track is located in the medial compartment of the knee prosthesis.

8. The improvement of claim 1 including a stabilizing mechanism for coupling the femoral component with the tibial component during flexion within a portion of the prescribed range of flexion, with the stabilizing mechanism enabling relative rotational movement between the femoral component and the tibial component about the longitudinal axis of rotation during articulation about the transverse axis of rotation, while the transverse axis of rotation is maintained essentially in the longitudinal plane, and the longitudinal plane is moved about the longitudinal axis of rotation, essentially at the predetermined distance from the longitudinal axis.

9. The improvement of claim 8 wherein the coronal plane is spaced posteriorly from the longitudinal axis of rotation, and the longitudinal plane rotates about the longitudinal axis of rotation along an arcuate path having a radius essentially equivalent to the predetermined distance during flexion within the prescribed range of flexion.

10. The improvement of claim 9 wherein the longitudinal plane is maintained essentially tangent to the arcuate path during flexion within the prescribed range of flexion.

11. The improvement of claim 8 wherein the prescribed range of flexion extends between about 0° of flexion and a predetermined degree of flexion of about 60° of flexion, and the portion of the prescribed range of flexion extends between about 45° of flexion and the predetermined degree of flexion.

12. The improvement of claim 8 wherein the stabilizing mechanism includes a post on one of the femoral component and the tibial component, the post having a cam surface, and a follower on the other of the femoral component and the tibial component for engaging the cam surface at least during articulation within the portion of the prescribed range of flexion.

13. The improvement of claim 12 wherein the post is on the tibial component for projecting in a superior direction toward the femoral component, and the follower is on the femoral component.

14. The improvement of claim 13 wherein the cam surface is located on a posterior aspect of the post, and the follower includes an anterior aspect for engaging the post along the cam surface.

15. The improvement of claim 14 wherein the generally coronal plane is tangent to the cam surface at the intersection between the coronal plane and the sagittal plane.

16. The improvement of claim 15 wherein the longitudinal plane is located so as to be tangent to the cam surface where the follower engages the post during articulation within the portion of the prescribed range of flexion.

17. The improvement of claim 16 wherein the prescribed range of flexion extends between about 0° of flexion and a predetermined degree of flexion of about 60° of flexion, and the portion of the prescribed range of flexion extends between about 45° of flexion and the predetermined degree of flexion.

18. The improvement of claim 17 wherein the relative rotational movement between the femoral component and the tibial component is about 6° during articulation within the prescribed range of flexion.

19. In a knee prosthesis for implantation to replace a natural knee joint and emulate movements of the natural knee joint during articulation, the knee prosthesis having a lateral compartment and a medial compartment, a femoral component including a lateral condylar element with a lateral condylar surface, a medial condylar element with a medial condylar surface, and a transverse axis of rotation, and a tibial component including a lateral articular surface for engagement with the lateral condylar surface of the femoral component in the lateral compartment and a medial articular surface for engagement with the medial condylar surface of the femoral component in the medial compartment for articulation of the knee prosthesis through flexion about the transverse axis of rotation:

an improvement wherein the condylar surfaces and the articular surfaces are configured for enabling engagement between the lateral condylar surface and the lateral articular surface at positions along a first generally arcuate track having a first center of curvature and between the medial condylar surface and the medial articular surface at positions along a second generally arcuate track having a second center of curvature during articulation about the transverse axis of rotation for flexion within at least a prescribed range of flexion extending up to a predetermined degree of flexion while enabling relative rotational movement between the femoral component and the tibial component to take place about a longitudinal axis of rotation, the first and second centers of curvature being placed in a common generally coronal plane, and the longitudinal axis of rotation being located essentially in a generally sagittal plane intersecting the coronal plane at an intersection and being spaced a predetermined distance from the intersection such that upon flexion within the pesecribed range of flexion the transverse axis of rotation will be maintained essentially in a generally medial-lateral longitudinal plane located in close proximity with the coronal plane, and the longitudinal plane spaced from the longitudinal axis of rotation essentially by the predetermined distance and movable about the longitudinal axis of rotation in response to relative rotational displacement between the femoral component and the tibial component, to intersect the coronal plane at angles corresponding to the relative rotational displacement during flexion within the prescribed range of flexion.

20. The improvement of claim 19 wherein the coronal plane is spaded posteriorly from the longitudinal axis of rotation, and the longitudinal plane rotates about the longitudinal axis of rotation along an arcuate path having a radius essentially equivalent to the predetermined distance during flexion within the prescribed range of flexion.

21. The improvement of claim 20 wherein the longitudinal plane is maintained essentially tangent to the arcuate path during flexion within the prescribed range of flexion.

22. The improvement of claim 19 wherein the prescribed range of flexion extends between about 0° of flexion and a predetermined degree of flexion of about 60° of flexion.

23. The improvement of claim 19 wherein the lateral and medial condylar surfaces and the lateral and medial articular surfaces are configured for enabling essentially congruent engagement at the positions along the generally arcuate track.

24. The improvement of claim 19 wherein the first center of curvature is located in the medial compartment and the second center of curvature is located in the lateral compartment.

25. The improvement of claim 19 including a stabilizing mechanism for coupling the femoral component with the tibial component during flexion within a portion of the prescribed range of flexion, with the stabilizing mechanism enabling relative rotational movement between the femoral component and the tibial component about the longitudinal axis of rotation during articulation about the transverse axis of rotation, while the transverse axis of rotation is maintained essentially in the longitudinal plane, and the longitudinal plane is moved about the longitudinal axis of rotation, essentially at the predetermined distance from the longitudinal axis of rotation.

26. The improvement of claim 25 wherein the coronal plane is spaced posteriorly from the longitudinal axis of rotation, and the longitudinal plane rotates about the longitudinal axis of rotation along an arcuate path having a radius essentially equivalent to the predetermined distance during flexion within the prescribed range of flexion.

27. The improvement of claim 26 wherein the longitudinal plane is maintained essentially tangent to the arcuate path during flexion within the prescribed range of flexion.

28. The improvement of claim 25 wherein the prescribed range of flexion extends between about 0° of flexion and a predetermined degree of flexion of about 60° of flexion, and the portion of the prescribed range of flexion extends between about 45° of flexion and the predetermined degree of flexion.

29. The improvement of claim 25 wherein the stabilizing mechanism includes a post on one of the femoral component and the tibial component, the post having a cam surface, and a follower on the other of the femoral component and the tibial component for engaging the cam surface at least during articulation within the portion of the prescribed range of flexion.

30. The improvement of claim 29 wherein the post is on the tibial component for projecting in a superior direction toward the femoral component, and the follower is on the femoral component.

31. The improvement of claim 30 wherein the cam surface is located on a posterior aspect of the post, and the follower includes an anterior aspect for engaging the post along the cam surface.

32. The improvement of claim 31 wherein the generally coronal plane is tangent to the cam surface at the intersection between the coronal plane and the sagittal plane.

33. The improvement of claim 32 wherein the longitudinal plane is located so as to be tangent to the cam surface where the follower engages the post during articulation within the portion of the prescribed range of flexion.

34. The improvement of claim 33 wherein the intersection between the coronal plane and the sagittal plane is located intermediate the first and second centers of curvature.

35. The improvement of claim 34 wherein the first and second centers of curvature are symmetrical about the intersection between the coronal plane and the sagittal plane.

36. The improvement of claim 35 wherein the intersection comprises a midpoint between the first and second centers of curvature.

37. The improvement of claim 36 wherein the prescribed range of flexion extends between about 0° of flexion and a predetermined degree of flexion of about 60° of flexion, and the portion of the prescribed range of flexion extends between about 45° of flexion and the predetermined degree of flexion.

38. The improvement of claim 37 wherein the relative rotational movement between the femoral component and the tibial component is about 6° during articulation within the prescribed range of flexion.

39. A method for emulating movements of a natural knee joint in a knee prosthesis upon implantation of the knee prosthesis to replace the natural knee joint, the natural knee joint having a lateral compartment and a medial compartment, the knee prosthesis including a femoral component having at least one condylar element with a condylar surface having a transverse axis of rotation and a tibial component including at least one articular surface for engagement with the condylar surface of the femoral component for articulation of the knee prosthesis through flexion about the transverse axis of rotation, the condylar surface and the articular surface being located in the one of the lateral and medial compartments upon implant of the knee prosthesis, the method comprising:
    enabling engagement between the condylar surface and the articular surface at positions along a generally arcuate track having a center of curvature;
    placing the center of curvature in a generally coronal plane;
    enabling relative rotational movement between the femoral component and the tibial component during articulation about the transverse axis of rotation for flexion within at least a prescribed range of flexion extending up to a predetermined degree of flexion while enabling relative rotational movement between the femoral component and the tibial component to take place about a longitudinal axis of rotation located essentially in a generally sagittal plane intersecting the coronal plane at an intersection and spaced a predetermined distance from the intersection; and
    maintaining the transverse axis of rotation in a generally medial-lateral longitudinal plane located in close proximity with the coronal plane, with the longitudinal plane spaced from the longitudinal axis of rotation essentially by the predetermined distance while moving the longitudinal plane about the longitudinal axis of rotation in response to relative rotational displacement between the femoral component and the tibial component, to intersect the coronal plane at angles corresponding to the relative rotational displacement during flexion within the prescribed range of flexion.

40. The improvement of claim 39 wherein the coronal plane is spaced posteriorly from the longitudinal axis of rotation, and the longitudinal plane is rotated about the longitudinal axis of rotation along an arcuate path having a radius essentially equivalent to the predetermined distance during flexion within the prescribed range of flexion.

41. The improvement of claim 40 wherein the longitudinal plane is maintained essentially tangent to the arcuate path during flexion within the prescribed range of flexion.

42. The method of claim 39 wherein engagement between the condylar surface and the articular surface is essentially congruent at the positions along the generally arcuate track.

43. The method of claim 39 including placing the canter of curvature in the other of the lateral and medial compartments.

44. The method of claim 39 wherein the prescribed range of flexion extends between about 0° of flexion and a predetermined degree of flexion of about 60° of flexion.

45. The method of claim 39 wherein the relative rotational movement between the femoral component and the tibial component is about 6° during articulation within the prescribed range of flexion.

46. The method of claim 45 including coupling the femoral component with the tibial component for rotational stability during flexion within a portion of the prescribed range of flexion, while enabling relative rotational movement between the femoral component and the tibial component about the longitudinal axis of rotation during articulation about the transverse axis of rotation, with the transverse axis of rotation maintained essentially in the longitudinal plane, and the longitudinal plane moving about the longitudinal axis of rotation, essentially at the predetermined distance from the longitudinal axis.

47. The improvement of claim 46 wherein the coronal plane is spaced posteriorly from the longitudinal axis of rotation, and the longitudinal plane is rotated about the longitudinal axis of rotation along an arcuate path having a radius essentially equivalent to the predetermined distance during flexion within the prescribed range of flexion.

48. The improvement of claim 47 wherein the longitudinal plane is maintained essentially tangent to the arcuate path during flexion within the prescribed range of flexion.

49. The method of claim 46 wherein the portion of the prescribed range of flexion extends between about 45° of flexion and about 60° of flexion.

50. A method for emulating movements of a natural knee joint in a knee prosthesis upon implantation of the knee prosthesis to replace the natural knee joint, the knee prosthesis having a lateral compartment and a medial compartment, a femoral component including a lateral condylar element with a lateral condylar surface, a medial condylar element with a medial condylar surface, and a transverse axis of rotation, and a tibial component including a lateral articular surface for engagement with the lateral condylar surface of the femoral component in the lateral compartment and a medial articular surface for engagement with the medial condylar surface of the femoral component in the medial compartment for articulation of the knee prosthesis through flexion about the transverse axis of rotation, the method comprising:

enabling engagement between the lateral condylar surface and the lateral articular surface along a first generally arcuate track having a first center of curvature;

enabling engagement between the medial condylar surface and the medial articular surface along a second generally arcuate track having a second center of curvature;

placing the first and second centers of curvature in a generally coronal plane;

enabling relative rotational movement between the femoral component and the tibial component during articulation about the transverse axis of rotation for flexion within at least a prescribed range of flexion extending up to a predetermined degree of flexion while enabling relative rotational movement between the femoral component and the tibial component to take place about a longitudinal axis of rotation located essentially in a generally sagittal plane intersecting the coronal plane at an intersection and spaced a predetermined distance from the intersection; and maintaining the transverse axis of rotation in a generally medial-lateral longitudinal plane located in close proximity with the coronal plane, with the longitudinal plans spaced from the longitudinal axis of rotation essentially the predetermined distance while moving the longitudinal plane about the longitudinal axis of rotation in response to relative rotational displacement between the femoral component and the tibial component, to intersect the coronal plane at angles corresponding to the relative rotational displacement during flexion within the prescribed range of flexion.

51. The improvement of claim 50 wherein the coronal plane is spaced posteriorly from the longitudinal axis of rotation, and the longitudinal plane is rotated about the longitudinal axis of rotation along an arcuate path having a radius essentially equivalent to the predetermined distance during flexion within the prescribed range of flexion.

52. The improvement of claim 51 wherein the longitudinal plane is maintained essentially tangent to the arcuate path during flexion within the prescribed range of flexion.

53. The method of claim 50 wherein the engagement between the lateral and medial condylar surfaces and the lateral and medial articular surfaces is essentially congruent at the positions along the first and second generally arcuate tracks.

54. The method of claim 50 including placing the first center of curvature in the medial compartment and placing the second center of curvature in the lateral compartment.

55. The method of claim 50 wherein the prescribed range of flexion extends between about 0° of flexion and a predetermined degree of flexion of about 60° of flexion.

56. The method of claim 55 wherein the relative rotational movement between the femoral component and the tibial component is about 6° during articulation within the prescribed range of flexion.

57. The method of claim 56 including coupling the femoral component with the tibial component for rotational stability during flexion within a portion of the prescribed range of flexion, while enabling relative rotational movement between the femoral component and the tibial component about the longitudinal axis of rotation during articulation about the transverse axis of rotation, with the transverse axis of rotation maintained essentially in the longitudinal plane, and the longitudinal plane moving about the longitudinal axis of rotation, essentially at the predetermined distance from the longitudinal axis.

58. The improvement of claim 57 wherein the coronal plane is spaced posteriorly from the longitudinal axis of rotation, and the longitudinal plane is rotated about the longitudinal axis of rotation along an arcuate path having a radius essentially equivalent to the predetermined distance during flexion within the prescribed range of flexion.

59. The improvement of claim 58 wherein the longitudinal plane is maintained essentially tangent to the arcuate path during flexion within the prescribed range of flexion.

60. The method of claim 57 wherein the portion of the prescribed range of flexion extends between about 45° of flexion and about 60° of flexion.

* * * * *